US011576393B2

(12) United States Patent
Hobel et al.

(10) Patent No.: US 11,576,393 B2
(45) Date of Patent: Feb. 14, 2023

(54) STERILE FILTERED LACTASE PREPARATION COMPRISING SALT WITH MONOVALENT CATION

(71) Applicant: Novozymes A/S, Bagsvaerd (DK)

(72) Inventors: Cedric Hobel, Lyngby (DK); Karen Jensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 586 days.

(21) Appl. No.: 16/473,118

(22) PCT Filed: Jan. 12, 2018

(86) PCT No.: PCT/EP2018/050758
§ 371 (c)(1),
(2) Date: Jun. 24, 2019

(87) PCT Pub. No.: WO2018/130654
PCT Pub. Date: Jul. 19, 2018

(65) Prior Publication Data
US 2020/0221721 A1    Jul. 16, 2020

(30) Foreign Application Priority Data

Jan. 13, 2017  (EP) .................................... 17151473
May 29, 2017  (EP) .................................... 17173248

(51) Int. Cl.
A23C 9/12      (2006.01)
A23C 9/13      (2006.01)
C12N 9/38      (2006.01)

(52) U.S. Cl.
CPC .......... *A23C 9/1206* (2013.01); *A23C 9/1322* (2013.01); *C12N 9/2471* (2013.01); *C12Y 302/01023* (2013.01); *C12Y 302/01108* (2013.01)

(58) Field of Classification Search
CPC .............. A23C 9/1238; A23Y 2220/15; A23Y 2220/29; A23Y 2240/75; C12Y 207/01002; C12Y 207/01006
USPC .......................................................... 426/43
See application file for complete search history.

(56) References Cited

U.S. PATENT DOCUMENTS

| 4,237,230 A | 12/1980 | Iida et al. |
| 4,464,469 A | 8/1984 | Parr et al. |
| 5,357,852 A | 10/1994 | Kohler et al. |
| 2011/0212221 A1* | 9/2011 | Beckhoven .......... A23C 9/1206 435/207 |
| 2011/0212222 A1 | 9/2011 | Beckhoven |
| 2017/0245513 A1 | 8/2017 | Ogasawara |

FOREIGN PATENT DOCUMENTS

| CN | 1916170 A | 2/2007 | |
| EP | 0145092 A2 | 6/1985 | |
| EP | 3187582 A1 | 7/2017 | |
| FR | 2500269 A1 | 8/1982 | |
| GB | 1477087 | 6/1977 | |
| WO | 02/081673 A1 | 10/2002 | |
| WO | 2009/071539 A1 | 6/2009 | |
| WO | 2013/084244 A1 | 6/2013 | |
| WO | 2014/184189 A2 | 11/2014 | |
| WO | WO-2014184189 A2 * | 11/2014 | ................ C12P 7/14 |
| WO | 2015/132349 A1 | 9/2015 | |
| WO | WO-2016031885 A1 * | 3/2016 | ............ B01D 65/10 |
| WO | 2016/071500 A1 | 5/2016 | |

OTHER PUBLICATIONS

Translation of WO-2016031885-A1 (Year: 2016).*
Flores et al., Lebensm.-Wiss. u.-Technol., vol. 29, No. 5, pp. 503-506 (1996).
Gnezdilova et al., Database FSTA, Accession No. FS-1979-09-L-0596 (1978).
Goulas et al., GenBank Accession No. ABF27152.1 (2007).
Jasewicz et al., Journal of Dairy Science, vol. 44, pp. 393-400 (1960).
Jieyan et al., Food & Fermentation Industries No. 3 (1991).
Kjaer, Declaration submitted in Opposition against EP 3568023 (2022).
Kollman et al., Journal of the American Chemical Society, vol. 97, No. 7, pp. 1640-1644 (1975).
Kurashima, Declaration submitted in Opposition against EP 3568023 (2022).
Lemos, Declaration submitted in Opposition against EP 3568023 (2022).
Liao et al., Annals New York Academy of Sciences, vol. 589, pp. 182-191 (1990).
Mahoney et al., Journal of Food Science, vol. 45, pp. 962-968 (1980).
Mahoney et al., Journal of Dairy Research, vol. 55, pp. 423-433 (1988).
Mahoney, Advanced Dairy Chemistry vol. 3, 2nd edition, pp. 77-125 (1997).
Modler et al., Bulletin of the IDF289, Chapter 12, pp. 57-61 (1993).
Neuhaus et al., Applied Biochemistry and Biotechnology, vol. 134, pp. 1-14 (2006).
Nguyen et al., J. Agric. Food Chern., vol. 54, No. 14, pp. 4989-4998 (2006).
Optiferm, Remittance notice from Godo Shusei (2015).
Ozawa, Order of Godo YNL2, order No. 3258/2015 (2015).
Patel et al., Appl. Microbiol. Biotechnol., vol. 22, pp. 114-120 (1985).
Rathore et al., BioPharm, vol. 21, Issue 4, pp. 1-5 (2008).
Sigma-Aldrich, Galactosidase, *Streptococcus pneumoniae*, Recombinant, *E. coli* (2008).
Tanaka et al., J. Biochem,, vol. 77, pp. 241-247 (1975).
Nebpage of Chr. Hansen announces NOLA Fit (2016).

(Continued)

*Primary Examiner* — Brent T O'Hern
(74) *Attorney, Agent, or Firm* — Yoshimi Barron

(57) ABSTRACT

The present invention relates to a sterile-filtered liquid lactase preparation and to a method of sterile filtering a liquid lactase preparation. At least 0.01% w/w of at least one salt having a monovalent cation is added in order to improve filterability. The system may further comprise a polyol stabilizer.

20 Claims, No Drawings

Specification includes a Sequence Listing.

(56) References Cited

OTHER PUBLICATIONS

Weiqun et al., Chinese Journal of Biotechnology, vol. 9, pp. 348-354 (1993).
Widmer et al., Eur. J. Biochem., vol. 100, pp. 559-567 (1979).
Wong et a.l, J. Dairy Sci., vol. 97, pp. 166-172 (2014).
Yuga, Report "Analysis of Na, K, and Ash in Lactase Preparations" (2021).
WO 2018-130654 A1—International Preliminary Report on Patentability.
Anonymous, Voedingsmiddelentechnologie, vol. 13, p. 23 (1980).
Abdelrahim, thesis entitled "Beta-Galactosidase from Psychrotrophic Bacillus subtilis" submitted to McGill University, Department of Food Science and Agricultural Chemistry (1989).
Abdelrahim, Evidence of publication date of Abdelrahim's thesis (2016).
Albuquerque et al., International Journal of Biological Macromolecules, vol. 191, pp. 881-898 (2021).
Anonymous, Glycerine Producers association. Physical Properties of Glycerine and its solutions, 1-27 (1963).
Anonymous, General tests and assays, FCC, fourth edition, 801-802 (1996).
Anonymous, GODO YNL2 Technical Guide (2000).
Anonymous, GODO YNL product description (2011).
Anonymous, Invoice Leche Pascual (2011).
Anonymous, Tetra Aldose Aseptic in-line dosing (2011).
Anonymous, Lactozyme Product data sheet (2012).
Anonymous, Final inspection record, lot No. 26033, 27026, 28022 (2014).
Anonymous, Maxilact flyer, DSM (2014).
Anonymous, Analysis report, Salt content 27005, 27006, 27007 (2015).
Anonymous, Aseptic dosing of heat-sensitive ingredients (2015).
Anonymous, GRAS notification 579 (2015).
Anonymous, Lot27018, 27017, Optiferm, Invoice, Bill of lading (2015).
Anonymous, Shipping instructions (2015).
Anonymous, GRAS Notice (GRN) No. 649 (2016).
Anonymous, portfolio Saphera (2016).
Anonymous, Saphera 2600L Dairy application sheet, Jul. 12, 2016 (2016).
Anonymous, Saphera 2600L Product Data sheet Mar. 31, 2016 (2016).
Anonymous, Saphera 2600L, product data sheet Jun. 16, 2016 (2016).
Anonymous, Saphera 900 LS, Product data sheet (2016).
Anonymous, GODO YNL2 Product Description (2017).
Anonymous, GODO's letter as filed in examination procedure (2018).
Anonymous, letter of Novozymes (patentee) to the European Patent Office (2020).
Anonymous, Report No. 21021 (2022).
Anonymous, YNL final inspection record, Lot27018 (2022).
Anonymous, Rockland beta galactosidase unconjugated 0000-17.
Athes et al., Journal of Molecular Catalysis B: Enzymatic, vol. 7, pp. 1-9 (1999).
Bosso et al., Food Science and Technology, vol. 36, No. 1, pp. 159-165 (2016).
Cavaille et al., Biotechnol. Appl. Biochem., vol. 22, pp. 55-64 (1995).
Chang et al., Journal of Dairy Research, vol. 56, pp. 117-127 (1989).
Chang et al., Journal of Dairy Research vol. 56, pp. 785-792 (1989).
Chen et al., J. Dairy Sci., vol. 91, pp. 1751-1758 (2008).
Dahlqvist et al., Journal of Dairy Research, vol. 44, pp. 541-548 (1977).
Dekker, Declaration (2020).
Dickson et al., Journal of Bacteriology, vol. 137, pp. 51-61 (1979).
Guy et al., J. Dairy Sci., vol. 61, pp. 147-151 (1978).
Howells, Declaration (2022).
Hussein et al., Journal of Food Protection, vol. 52, pp. 30-34 (1988).
Jacober-Pivarnik et al., Journal of Food Science, vol. 49, pp. 435-438 and 445 (1984).

\* cited by examiner

SEQUENCE LISTING

<160> NUMBER OF SEQ ID NOS: 1

<210> SEQ ID NO 1
<211> LENGTH: 1304
<212> TYPE: PRT
<213> ORGANISM: Bifidobacterium bifidum

<400> SEQUENCE: 1

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asn Val Thr Met
        195                 200                 205

Asn Leu Thr Thr Lys Val Ala Asn Asp Thr Lys Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365
```

-continued

```
Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ala Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
```

```
                785                 790                 795                 800
      Ile Val Pro Asp Ala Ala Asn Arg Val Thr Phe Asp Val Lys Gly Ala
                      805                 810                 815

Gly Lys Leu Val Gly Val Asp Asn Gly Ser Ser Pro Asp His Asp Ser
                      820                 825                 830

Tyr Gln Ala Asp Asn Arg Lys Ala Phe Ser Gly Lys Val Leu Ala Ile
                      835                 840                 845

Val Gln Ser Thr Lys Glu Ala Gly Glu Ile Thr Val Thr Ala Lys Ala
              850                 855                 860

Asp Gly Leu Gln Ser Ser Thr Val Lys Ile Ala Thr Thr Ala Val Pro
      865                 870                 875                 880

Gly Thr Ser Thr Glu Lys Thr Val Arg Ser Phe Tyr Tyr Ser Arg Asn
                      885                 890                 895

Tyr Tyr Val Lys Thr Gly Asn Lys Pro Ile Leu Pro Ser Asp Val Glu
                      900                 905                 910

Val Arg Tyr Ser Asp Gly Thr Ser Asp Arg Gln Asn Val Thr Trp Asp
                      915                 920                 925

Ala Val Ser Asp Asp Gln Ile Ala Lys Ala Gly Ser Phe Ser Val Ala
              930                 935                 940

Gly Thr Val Ala Gly Gln Lys Ile Ser Val Arg Val Thr Met Ile Asp
      945                 950                 955                 960

Glu Ile Gly Ala Leu Leu Asn Tyr Ser Ala Ser Thr Pro Val Gly Thr
                      965                 970                 975

Pro Ala Val Leu Pro Gly Ser Arg Pro Ala Val Leu Pro Asp Gly Thr
                      980                 985                 990

Val Thr Ser Ala Asn Phe Ala Val Asp Trp Thr Lys Pro Ala Asp Thr
              995                 1000                1005

Val Tyr Asn Thr Ala Gly Thr Val Lys Val Pro Gly Thr Ala Thr
              1010                1015                1020

Val Phe Gly Lys Glu Phe Lys Val Thr Ala Thr Ile Arg Val Gln
              1025                1030                1035

Arg Ser Gln Val Thr Ile Gly Ser Ser Val Ser Gly Asn Ala Leu
              1040                1045                1050

Arg Leu Thr Gln Asn Ile Pro Ala Asp Lys Gln Ser Asp Thr Leu
              1055                1060                1065

Asp Ala Ile Lys Asp Gly Ser Thr Thr Val Asp Ala Asn Thr Gly
              1070                1075                1080

Gly Gly Ala Asn Pro Ser Ala Trp Thr Asn Trp Ala Tyr Ser Lys
              1085                1090                1095

Ala Gly His Asn Thr Ala Glu Ile Thr Phe Glu Tyr Ala Thr Glu
              1100                1105                1110

Gln Gln Leu Gly Gln Ile Val Met Tyr Phe Phe Arg Asp Ser Asn
              1115                1120                1125

Ala Val Arg Phe Pro Asp Ala Gly Lys Thr Lys Ile Gln Ile Ser
              1130                1135                1140

Ala Asp Gly Lys Asn Trp Thr Asp Leu Ala Ala Thr Glu Thr Ile
              1145                1150                1155

Ala Ala Gln Glu Ser Ser Glu Arg Val Leu Pro Tyr Thr Tyr Asp
              1160                1165                1170

Phe Ala Pro Val Gly Ala Thr Phe Val Lys Val Thr Val Thr Asn
              1175                1180                1185

Ala Asp Thr Thr Thr Pro Ser Gly Val Val Cys Ala Gly Leu Thr
              1190                1195                1200
```

-continued

```
Glu Ile Glu Leu Lys Thr Ala Thr Ser Lys Phe Val Thr Asn Thr
    1205                1210            1215
Ser Ala Ala Leu Ser Ser Leu Thr Val Asn Gly Thr Lys Val Ser
    1220            1225            1230
Asp Ser Val Leu Ala Ala Gly Ser Tyr Asn Thr Pro Ala Ile Ile
    1235            1240            1245
Ala Asp Val Lys Ala Glu Gly Glu Gly Asn Ala Ser Val Thr Val
    1250            1255            1260
Leu Pro Ala His Asp Asn Val Ile Arg Val Ile Thr Glu Ser Glu
    1265            1270            1275
Asp His Val Thr Arg Lys Thr Phe Thr Ile Asn Leu Gly Thr Glu
    1280            1285            1290
Gln Glu Phe Pro Ala Asp Ser Asp Glu Arg Asp
    1295            1300
```

STERILE FILTERED LACTASE PREPARATION COMPRISING SALT WITH MONOVALENT CATION

CROSS-REFERENCE TO RELATED APPLICATIONS

This application is a 35 U.S.C. 371 national application of international application no. PCT/EP2018/050758 filed Jan. 12, 2018, which claims priority or the benefit under 35 U.S.C. 119 of European application nos. 17151473.0 and 17173248.0 filed Jan. 13, 2017 and May 29, 2017, respectively. The content of each application is fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to sterile filtration of a liquid lactase preparation.

BACKGROUND OF THE INVENTION

Lactase enzymes, which are also sometimes referred to as beta-galactosidase enzymes, are used commercially to break down lactose in milk to produce dairy products which are suitable for people with lactose intolerance and/or have a sweeter taste. Lactases have been isolated from a large variety of organisms, including microorganisms, such as yeast and bacteria.

WO 2009/071539 discloses use of a C-terminally truncated fragment of the extracellular lactase from *Bifidobacterium bifidum* in the production of low-lactose dairy products.

Lactase may be added to milk either before or after pasteurisation or sterilization. In general lactase will be inactivated during pasteurisation or sterilization treatment. When lactase is added before sterilization, a large amount of lactase may be required in order to reduce the storage time between addition and pasteurisation/sterilization. Alternatively, lactase may be added after pasteurisation/sterilization of the milk. In this case, lactase may be added in a lower amount, as the enzyme can digest lactose during transport and storage in the factory, shop and/or in the refrigerator of the consumer. Lactase to be added after pasteurisation/sterilization of the milk has to be sterile. One preferred way of sterilizing lactase is by sterile filtration. Sterile filtration of the lactase may be performed in-line within the production process of the lactose-free milk, for example using the Aldose® system (Tetrapak International S. A., Pully, Switzerland), or it may be performed at the production site of the lactase manufacturer. The sterile lactase solution is then dosed aseptically into the milk, for instance by means of the Flexdos® system (Tetrapak International S. A., Pully, Switzerland). Sterile filtration of the lactase solution is achieved by pumping the enzyme concentrate through a at least one filter with an absolute pore size of 0.22 µm, and that will retain particles such as fungi, bacteria, spores still present in the solution. Prior to passing through the sterile filters, the solution may be pumped through one or several pre-filters with a larger pore size than 0.22 µm and that will retain large particle but will not contribute to sterility of the lactase solution.

Commercial lactase preparations used by the dairy processing industry are often aqueous solution to which one or more stabilizing agents have been added, such as glycerol. Glycerol promotes microbial as well as enzymatic stabilization. Lactase preparations comprising, e.g., 50% glycerol are somewhat viscous and may not be treated easily through sterile filters.

Improved formulations of sterile lactase are still needed, e.g., liquid formulations which can be more easily processed through sterile filters.

WO2015/132349 discloses use of e.g. sodium chloride in an aqueous liquid lactase formulation. WO2016/071500 discloses use of e.g. sodium chloride in a spray-dried composition of a beta-galactosidase enzyme. Possible ultrafiltration of the enzyme-containing fermentation broth is suggested as a possible means for concentrating the enzyme prior to its formulation. Sterile filtration is not mentioned in any of these disclosures.

SUMMARY OF THE INVENTION

The present inventors have surprisingly found that addition of salt to a liquid lactase preparation improves its ability to be passed through a sterile filter. In particular, it is surprising that addition of monovalent cation to a liquid lactase preparation improves its ability to be passed through a sterile filter.

The invention therefore provides a sterile-filtered liquid lactase preparation comprising at least one salt having a monovalent or divalent cation, wherein the total concentration of said at least one salt is at least 0.01% w/w.

The invention in one embodiment provides a sterile-filtered liquid lactase preparation comprising at least one salt having a monovalent cation, wherein the total concentration of said at least one salt is at least 0.01% w/w.

The invention further provides a method of sterile filtering a liquid lactase preparation, which comprises the steps of:
a. providing a liquid lactase preparation comprising at least one salt having a monovalent or divalent cation, wherein the total concentration of said at least one salt is at least 0.01% w/w, and
b. sterile filtering said lactase preparation.

The invention further provides a method of sterile filtering a liquid lactase preparation, which comprises the steps of:
a. providing a liquid lactase preparation,
b. adding to said liquid lactase preparation at least one salt having a monovalent or divalent cation, wherein the at least one salt is added at a concentration of at least 0.01% w/w of the lactase preparation which is to be sterile filtered, and
c. sterile filtering the lactase preparation obtained in step b.

The invention further provides a method of sterile filtering a liquid lactase preparation, which comprises the steps of:
a. providing a liquid lactase preparation comprising at least one salt having a monovalent cation, wherein the total concentration of said at least one salt is at least 0.01% w/w, and
b. sterile filtering said lactase preparation.

The invention further provides a method of sterile filtering a liquid lactase preparation, which comprises the steps of:
a. providing a liquid lactase preparation,
b. adding to said liquid lactase preparation at least one salt having a monovalent cation, wherein the at least one salt is added at a concentration of at least 0.01% w/w of the lactase preparation which is to be sterile filtered, and c. sterile filtering the lactase preparation obtained in step b.

The invention further provides a method of improving the filterability of a liquid lactase preparation, which comprises addition to the lactase preparation of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, wherein the salt is added at a concentration of at least 0.01% w/w of the lactase preparation.

Finally, the invention provides the use of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, for improving the filterability of a liquid lactase preparation.

DETAILED DESCRIPTION OF THE INVENTION

The present invention provides a sterile-filtered liquid lactase preparation comprising at least one salt having a monovalent or divalent cation, wherein the total concentration of said at least one salt is at least 0.01% w/w.

The salt may be any salt having a monovalent or divalent cation. The lactase preparation may comprise more than one salt having a monovalent or divalent cation. In that case, the feature of at least 0.01% w/w refers to the combined concentrations of the individual salts.

The skilled person will know how to determine the individual concentrations of each salt having a monovalent or divalent cation. It may be determined, e.g., by inductive coupled plasma optical emission spectrometry (ICP-OES). The associated anions may be determined by e.g. Dionex™ ion chromatography (Dionex™-IC; Thermo Scientific™, Waltham, Mass., USA).

The liquid lactase preparation of the invention is an aqueous liquid lactase preparation and may be any composition or solution comprising water. The preparation may comprise, e.g., at least 20% w/w of water, such as at least 30% w/w, at least 40% w/w or at least 50% w/w of water.

"Sterile-filtered" in the context of the present invention means that the liquid lactase preparation has been passed through a sterile filter, preferably a sterile filter with an absolute pore size of about 0.22 µm. More preferably, the sterile filter is membrane-based and is manufactured using either hydrophilic polyvinylidene fluoride (PVDF) or hydrophilic polyethersulfone (PES).

The at least one salt may be a salt of $Na^+$, $K^+$, $NH_4^+$ or $Mg^{++}$ (also referred to herein as $Mg^{2+}$), preferably $Na^+$ or $K^+$, more preferably $Na^+$. The at least one salt may be selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, more preferably NaCl.

The at least one salt may be a salt which is approved for use in food in at least EU.

The total final concentration of the at least one salt may be at least 0.01% w/w, preferably at least 0.015% w/w, more preferably at least 0.02% w/w such as at least 0.1% w/w.

The total final concentration of the at least one salt may be 0.01-5% w/w, preferably 0.015-4% w/w, more preferably 0.02-3% w/w or 0.1-2% w/w.

In further embodiments, the total final concentration of the at least one salt may be in the range from 0.01-5%, such as 0.01-4.5%, for example 0.01-4.2%, such as 0.01-3.5%, or for example 0.01-1.5%; or for example in the range from 0.01-5%%, such as 0.05-5%, 0.1-5%, 0.5-5%, 0.8-5%, 1.2-5%, 2-5% or for example in the range from 0.5-5%, such as 0.5-4%, or 0.6-3.8%, such as 0.7-3.5%, for example 0.7-3%, such as 0.7-2.5% or for example 0.8-2%, or 0.8-1.5% or for example 1.2-3%, such as 1.3-3% or 1.3 to 2%, in particular 0.8-1.5% or 1.3 to 2%, all percentages being w/w.

The present invention further provides a sterile-filtered liquid lactase preparation comprising at least one salt having a monovalent cation, wherein the total concentration of said at least one salt is at least 0.01% w/w.

The salt may be any salt having a monovalent cation. The lactase preparation may comprise more than one salt having a monovalent cation. Also in this case, the feature of at least 0.01% w/w refers to the combined concentrations of the individual salts.

The at least one salt having a monovalent cation may be a salt of Na+, K+ or NH4+.

The at least one salt having a monovalent cation may be selected among NaCl, KCl, $NH_4Cl$, $Na_2SO_4$, $K_2SO_4$, $(NH_4)_2SO_4$, or a combination thereof, preferably, NaCl, KCl, $(NH_4)_2SO_4$, $Na_2SO_4$ or a combination thereof, more preferably NaCl.

The liquid lactase preparation according to the invention may comprise at least one salt having a monovalent cation, as well as further comprising at least one salt having a divalent cation. Also in this case, the feature of at least 0.01% w/w refers to the combined concentrations of the individual salts.

A particular embodiment relates to a liquid lactase preparation according to the invention comprising at least one salt having a monovalent cation, and further comprising at least one salt having a divalent cation, preferably at least one salt of $Mg^{++}$.

The concentration of lactase in the lactase preparation of the invention may be anywhere between 10 and 5000 LAU-B/g, such as 20-2600 LAU-B/g, 30-2000 LAU-B/g, 50-1300 LAU-B/g or 200-1300 LAU-B/g.

In the context of the present invention, the activity in LAU-B/g of a specific lactase may be determined by direct measurement of o-nitrophenyl (ONP) released from o-nitrophenyl β-D-galactopyranoside (ONPG) in a buffer containing 1.46 mg/ml substrate in 0.05 M MES, 1 mM $MgSO_4$ $7H_2O$, 450 mg/L Brij 35 at pH 6.5 and 30° C. After 600 seconds incubation, the reaction is stopped by adding 0.2 M $Na_2CO_3$ and the released ONP is measured at 405 nm after 126 seconds incubation. The skilled person will know how to execute this assay and determine such activity. Here, the activity is obtained by comparing to a standard curve run with a lactase of known activity, and the activity of the unknown sample calculated from this. The lactase of known activity may, e.g., be Saphera® obtained from Novozymes A/S, Denmark.

A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108. Enzymes assigned to other subclasses, such as, e.g., EC 3.2.1.23, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity.

The lactase may be of animal, of plant or of microbial origin. Preferred enzymes are obtained from microbial sources, in particular from a filamentous fungus or yeast, or from a bacterium.

In a preferred embodiment, the lactase is obtained from a bacterium, e.g. from the family Bifidobacteriaceae, such as from the genus *Bifidobacterium*, such as from a strain of *B. bifidum*, *B. animalis* or *B. longum*. In a more preferred embodiment, the lactase is obtained from *Bifidobacterium bifidum*.

In another preferred embodiment, the lactase is a C-terminally truncated form of a lactase obtained from the family Bifidobacteriaceae, such as from the genus *Bifidobacterium*, such as from a strain of *B. bifidum*, *B. animalis* or *B. longum*. In a more preferred embodiment, the lactase is a C-terminally truncated form of a lactase obtained from *Bifidobacterium bifidum*.

A preferred enzyme is a lactase having a sequence which is at least 50%, such as at least 60%, at least 70%, at least 75%, at least 80%, at least 85%, at least 90%, at least 95%, at least 96%, at least 97%, at least 98%, at least 99% or 100% identical to SEQ ID NO: 1 or to a lactase active fragment thereof. Such lactase active fragment of SEQ ID NO: 1 may be any fragment of SEQ ID NO: 1 having lactase activity.

For purposes of the present invention, the degree of identity between two amino acid sequences is determined using the Needleman-Wunsch algorithm (Needleman and Wunsch (1970) J. Mol. Biol. 48: 443-453) as implemented in the Needle program of the EMBOSS package (EMBOSS: The European Molecular Biology Open Software Suite, Rice et al. (2000) Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labelled "longest identity" (obtained using the—no brief option) is used as the percent identity and is calculated as follows:

(Identical Residues×100)/(Length of Alignment–
Total Number of Gaps in Alignment)

The lactase may have a C-terminal end corresponding to amino acid 1304 of SEQ ID NO: 1.

Alternatively, the lactase may be a fragment which is at least 50%, such as at least 60%, at least 70%, at least 75%, at least 80%, at least 85%, at least 90%, at least 95%, at least 96%, at least 97%, at least 98%, at least 99% or 100% identical to a lactase active fragment of SEQ ID NO: 1. It may be a fragment having a C-terminal end corresponding to amino acid 887 of SEQ ID NO: 1. Or it may be a fragment having a C-terminal end corresponding to amino acid 965 of SEQ ID NO: 1. Or it may be a fragment having a C-terminal end corresponding to amino acid 1038 of SEQ ID NO: 1. Or it may be a fragment having a C-terminal end corresponding to amino acid 1142, 1211 or 1296 of SEQ ID NO: 1.

The lactase may be extracellular. It may have a signal sequence at its N-terminus, which is cleaved off during secretion.

The lactase may be obtained from any organism. The term "obtained from" means in this context that the enzyme may have been isolated from an organism where it is present natively, i.e. the identity of the amino acid sequence of the enzyme are identical to a native enzyme. The term "obtained" also means that the enzymes may have been produced recombinantly in a host organism, the recombinantly produced enzyme having either an identity identical to a native enzyme or having a modified amino acid sequence, e.g. having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "obtained from" includes enzymes produced synthetically by, e.g., peptide synthesis. The term "obtained from" also encompasses enzymes which have been modified e.g. by glycosylation, phosphorylation etc., whether in vivo or in vitro. With respect to recombinantly produced enzyme the term "obtained from" refers to the identity of the enzyme and not the identity of the host organism in which it is produced recombinantly.

The lactase may be produced from a microorganism by use of any suitable technique. For instance, a lactase enzyme preparation may be produced by fermentation of a suitable microorganism and subsequent isolation of a lactase preparation from the resulting fermented broth or microorganism by methods known in the art. The lactase may also be produced by use of recombinant DNA techniques. Such method normally comprises cultivation of a host cell transformed with a recombinant DNA vector comprising a DNA sequence encoding the lactase in question and the DNA sequence being operationally linked with an appropriate expression signal such that it is capable of expressing the lactase in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

The lactase may be purified. The term "purified" as used herein covers lactase enzyme protein essentially free from insoluble components from the production organism. The term "purified" also covers lactase enzyme protein essentially free from insoluble components from the native organism from which it is obtained. Preferably, it is also separated from some of the soluble components of the organism and culture medium from which it is derived. More preferably, it is separated by one or more of the unit operations: filtration, precipitation, or chromatography.

Accordingly, the lactase may be purified, viz. only minor amounts of other proteins being present. The expression "other proteins" relate in particular to other enzymes. The term "purified" as used herein also refers to removal of other components, particularly other proteins and most particularly other enzymes present in the cell of origin of the lactase. The lactase may be "substantially pure", i.e. substantially free from other components from the organism in which it is produced, i.e., e.g., a host organism for recombinantly produced lactase.

The lactase in the preparation is preferably a neutral lactase. The neutral lactase preferably is active, or has its optimal activity, at a pH between pH 4 and pH 8, preferably between pH 5 and pH 7.

The lactase is preferably an extracellular produced neutral lactase.

The lactase in the preparation of the invention may be obtained as an optionally concentrated extract e.g. from a fungal, a yeast or a bacterial production strain. Preferably such extract has undergone a solid-liquid separation step, by e.g. centrifugation or filtration, to remove the solids. Such extract may contain natural components from the production cells as well as remainders of the fermentation media. Examples of such components are nucleic acid, protein, residual sugars, oligosaccharides, intrinsic enzymes, salts, minerals, intracellular components, ions, and nucleotides or other components. These components may end up, to some extent, in the lactase preparation of the invention.

The lactase in the preparation of the invention may be a concentrated non-purified lactase or it may have been purified. A concentrated non-purified lactase may have been obtained by releasing the enzyme from the host cells, removing the solids for instance by means of filtration or centrifugation and by concentrating the liquid phase comprising the lactase by means of for instance ultrafiltration. Alternatively, the lactase may have been purified, for example by using chromatography.

The pH of a lactase preparation of the invention may be in the range of pH 4-9, such as pH 5-8 or pH 5.5-7.5.

The lactase preparation of the invention is preferably enzymatically stable, more preferably microbially and enzymatically stable.

The lactase preparation of the invention may comprise at least one stabilizing formulation chemical at a concentration of 10-70% w/w, preferably 30-60% w/w. The stabilizing formulation chemical may be a polyol, preferably a polyol selected among glycerol, sorbitol, monopropylene glycol, sucrose, glucose, galactose or lactose, or combinations thereof, more preferably glycerol.

Particular embodiments of the invention relate to a sterile-filtered liquid lactase preparation comprising at least one salt having a monovalent cation, wherein the total concentration of said at least one salt is at least 0.01% w/w, further wherein said preparation comprises a stabilizing formulation chemical as described above. Further particular embodiments of the invention relate to a sterile-filtered liquid lactase preparation comprising at least one salt having a monovalent cation as well as at least one salt having a divalent cation, wherein the total concentration of said salts is at least 0.01% w/w; further wherein said preparation comprises a stabilizing formulation chemical as described above.

The present invention also provides a method of sterile filtering a liquid lactase preparation, which comprises the steps of:
  a. providing a liquid lactase preparation comprising at least one salt having a monovalent or divalent cation, wherein the total concentration of said at least one salt is at least 0.01% w/w, and
  b. sterile filtering said lactase preparation.

The salt may be any salt having a monovalent or divalent cation. The lactase preparation to be used in a method of the invention may comprise more than one salt having a monovalent or divalent cation. In that case, the feature of at least 0.01% w/w refers to the combined concentrations of the individual salts. The liquid lactase preparation to be used in a method of the invention is an aqueous liquid lactase preparation and may be any composition or solution comprising water. The preparation may comprise, e.g., at least 20% w/w of water, such as at least 30% w/w, at least 40% w/w or at least 50% w/w of water.

The at least one salt may be a salt of $Na^+$, $K^+$, $NH_4^+$ or $Mg^{++}$, preferably $Na^+$ or $K^+$, more preferably $Na^+$.

The at least one salt may be selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, more preferably NaCl.

The total final concentration of the at least one salt may be at least 0.01% w/w, preferably at least 0.015% w/w, more preferably at least 0.02% w/w such as at least 0.1% w/w.

The total final concentration of the at least one salt may be 0.01-5% w/w, preferably 0.015-4% w/w, more preferably 0.02-3% w/w or 0.1-2% w/w.

The present invention also provides a method of sterile filtering a liquid lactase preparation, which comprises the steps of:
  a. providing a liquid lactase preparation comprising at least one salt having a monovalent cation, wherein the total concentration of said at least one salt is at least 0.01% w/w, and
  b. sterile filtering said lactase preparation.

The at least one salt having a monovalent cation may be any salt having a monovalent cation, such as selected from a salt of $Na^+$, $K^+$ or $NH_4^+$. In some embodiments, the at least one salt having a monovalent ion may be selected among NaCl, KCl, NH4Cl, Na2SO4, K2SO4, (NH4)2SO4, or a combination thereof, preferably, NaCl, KCl, (NH4)2SO4, Na2SO4 or a combination thereof, more preferably NaCl.

The lactase preparation to be used in a method of the invention may comprise more than one salt having a monovalent cation. In that case, the feature of at least 0.01% w/w refers to the combined concentrations of the individual salts.

The liquid lactase preparation to be used in a method of the invention may comprise at least one salt having a monovalent cation, as well as at least one salt having a divalent cation. Also in this case, the feature of at least 0.01% w/w refers to the combined concentrations of the individual salts.

A particular embodiment relates to a liquid lactase to be used in the method of the invention, said lactase comprising at least one salt having a monovalent cation, and further comprising at least one salt having a divalent cation, preferably at least one salt of $Mg^{++}$.

A particular embodiment relates to a liquid lactase to be used in the method of the invention, said lactase comprising at least one salt having a monovalent cation, and at least one salt having a divalent cation, preferably at least one salt of $Mg^{++}$, and further comprising at least one stabilizing formulation chemical as described above.

The concentration of lactase in the lactase preparation to be used in a method of the invention may be anywhere between 10 and 5000 LAU-B/g, such as 20-2600 LAU-B/g, 30-2000 LAU-B/g, 50-1300 LAU-B/g or 200-1300 LAU-B/g.

In a preferred embodiment, the lactase to be used in a method of the invention is obtained from a bacterium, e.g. from the family Bifidobacteriaceae, such as from the genus *Bifidobacterium*, such as from a strain of *B. bifidum, B. animalis* or *B. longum*. In a more preferred embodiment, the lactase is obtained from *Bifidobacterium bifidum*.

In another preferred embodiment, the lactase is a C-terminally truncated form of a lactase obtained from the family Bifidobacteriaceae, such as from the genus *Bifidobacterium*, such as from a strain of *B. bifidum, B. animalis* or *B. longum*. In a more preferred embodiment, the lactase is a C-terminally truncated form of a lactase obtained from *Bifidobacterium bifidum*.

A preferred enzyme is a lactase having a sequence which is at least 50%, such as at least 60%, at least 70%, at least 75%, at least 80%, at least 85%, at least 90%, at least 95%, at least 96%, at least 97%, at least 98%, at least 99% or 100% identical to SEQ ID NO: 1 or to a lactase active fragment thereof. Such lactase active fragment of SEQ ID NO: 1 may be any fragment of SEQ ID NO: 1 having lactase activity.

The lactase may have a C-terminal end corresponding to amino acid 1304 of SEQ ID NO: 1.

The lactase may be extracellular. It may have a signal sequence at its N-terminus, which is cleaved off during secretion.

The lactase in the preparation to be used in a method of the invention is preferably a neutral lactase. The neutral lactase preferably is active, or has its optimal activity, at a pH between pH 4 and pH 8, preferably between pH 5 and pH 7.

The lactase to be used in a method of the invention is preferably an extracellular produced neutral lactase.

The lactase preparation to be used in a method of the invention may comprise a stabilizing formulation chemical at a concentration of 10-70% w/w, preferably 30-60% w/w. The stabilizing formulation chemical may be a polyol, preferably a polyol selected among glycerol, sorbitol, monopropylene glycol, sucrose, glucose, galactose or lactose, more preferably glycerol.

Sterile filtering of the lactase preparation may be performed according to standard operational procedures known to the skilled person either by keeping the feed flow of the lactase solution to the sterile filter constant, or by keeping the transmembrane pressure (TMP) in the filter system constant; the filtration regime with a constant TMP should be preferred, following general recommendations from filter manufacturers. When performing a sterile filtration under constant TMP regime and as the filter accumulates unwanted particles larger than the filter cut-off, the feed flow of enzyme solution to the filter will have to be gradually decreased according to procedures known to the skilled person.

Sterile filtration may be performed in-line within a production process of a dairy product.

Alternatively, sterile filtration may be performed prior to addition of the lactase preparation to the dairy product, in which case the sterile lactase solution is dosed aseptically into the milk.

The lactase preparation obtained from the enzyme supplier may be diluted with, e.g., water prior to its addition to the dairy product. If sterile filtration is performed in-line within a production process of a dairy product, the lactase preparation obtained from the enzyme supplier may be diluted prior to the sterile filtration. If the salt concentration in the lactase preparation obtained from the enzyme supplier is sufficiently high, even after dilution enough salt will be present to improve the sterile filterability.

A lactase preparation to be used in a method of the invention preferably has an improved filterability. Preferably, the lactase preparation to be used in a method of the invention has an improved filterability compared to a second liquid lactase preparation having the same composition except that it does not comprise the at least one salt.

Improved filterability may be determined as described in Example 1 of the present application.

In one embodiment, "improved filterability" means that the amount of sterile lactase obtained per a defined unit of time, under constant TMP filtration regime or constant feed flow filtration regime, is relatively larger than for a standard liquid lactase preparation.

In one embodiment, the lactase preparation to be used in a method of the invention has an improved filterability compared to a second liquid lactase preparation having the same composition except that it does not comprise the at least one salt, where improved filterability is defined as a larger amount of filtrate obtained per a defined unit of time, e.g. 600 seconds, and under either constant TMP or constant feed flow filtration regime compared to the second liquid lactase preparation.

In another embodiment, the lactase preparation to be used in a method of the invention has an improved filterability compared to a second liquid lactase preparation having the same composition except that it does not comprise the at least one salt, where improved filterability is defined as a larger amount of filtrate obtained per a defined unit of time, e.g. 600 seconds, and under constant TMP filtration regime compared to the second liquid lactase preparation.

In another embodiment, the lactase preparation to be used in a method of the invention has an improved filterability compared to a second liquid lactase preparation having the same composition except that it does not comprise the at least one salt, where improved filterability is defined as a larger amount of filtrate obtained per a defined unit of time, e.g. 600 seconds, and under constant feed flow filtration regime compared to the second liquid lactase preparation.

The present invention also provides a method of sterile filtering a liquid lactase preparation, which comprises the steps of:
  a. providing a liquid lactase preparation,
  b. adding to said liquid lactase preparation at least one salt having a monovalent or divalent cation, wherein the at least one salt is added at a concentration of at least 0.01% w/w of the lactase preparation which is to be sterile filtered, and
  c. sterile filtering the lactase preparation obtained in step b.

In the method of the invention where in step b. at least one salt is added to the lactase preparation at a concentration of at least 0.01% w/w of the lactase preparation which is to be sterile filtered, the at least 0.01% w/w refers to the amount of added salt and is not including any possible carry-over from production of the lactase.

The present invention also provides a method of improving the filterability of a liquid lactase preparation, which comprises addition to the lactase preparation of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, wherein the salt is added at a concentration of at least 0.01% w/w of the lactase preparation.

The present invention also provides the use of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, for improving the filterability of a liquid lactase preparation.

The present invention also provides a method of sterile filtering a liquid lactase preparation, which comprises the steps of:
  a. providing a liquid lactase preparation,
  b. adding to said liquid lactase preparation at least one salt having a monovalent cation, wherein the at least one salt is added at a concentration of at least 0.01% w/w of the lactase preparation which is to be sterile filtered, and
  c. sterile filtering the lactase preparation obtained in step b.

In the method of the invention where in step b. at least one salt is added to the lactase preparation at a concentration of at least 0.01% w/w of the lactase preparation which is to be sterile filtered, the at least 0.01% w/w refers to the amount of added salt and is not including any possible carry-over from production of the lactase.

PREFERRED EMBODIMENTS

1. A sterile-filtered liquid lactase preparation comprising at least one salt having a monovalent or divalent cation, wherein the total concentration of said at least one salt is at least 0.01% w/w.
2. The liquid lactase preparation of embodiment 1, wherein the salt is a salt of $Na^+$, $K^+$, $NH_4^+$ or $Mg^{++}$.
3. The liquid lactase preparation of embodiment 1, wherein the salt is selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, more preferably NaCl.
4. The liquid lactase preparation of any of the preceding embodiments, wherein the total concentration of the at least one salt is 0.01-5% w/w, preferably 0.015-4% w/w, more preferably 0.02-3% w/w or 0.1-2% w/w.
5. The liquid lactase preparation of any of the preceding embodiments, said lactase preparation having a lactase activity of 10-5000 LAU-B/g.
6. The liquid lactase preparation of any of the preceding embodiments, wherein the lactase has an amino acid sequence which is at least 50% identical to SEQ ID NO: 1.
7. The liquid lactase preparation of any of the preceding embodiments, wherein the lactase is a C-terminally truncated form of a lactase obtained from *Bifidobacterium*, preferably *Bifidobacterium bifidum*.
8. The liquid lactase preparation of any of the preceding embodiments, wherein the lactase has a C-terminal end corresponding to amino acid 1304 of SEQ ID NO: 1.
9. The liquid lactase preparation of any of the preceding embodiments which further comprises a stabilizing formulation chemical at a concentration of 10-70% w/w, preferably 30-60% w/w.
10. The liquid lactase preparation of the preceding embodiment, wherein the stabilizing formulation chemical is a polyol, preferably a polyol selected among glycerol, sorbitol, monopropylene glycol, sucrose, glucose, galactose or lactose, more preferably glycerol.
11. A method of sterile filtering a liquid lactase preparation, which comprises the steps of:
   a. providing a liquid lactase preparation comprising at least one salt having a monovalent or divalent cation, wherein the total concentration of said at least one salt is at least 0.01% w/w, and
   b. sterile filtering said lactase preparation.
12. The method of embodiment 11, wherein the salt is a salt of $Na^+$, $K^+$, $NH_4^+$ or $Mg^{++}$.
13. The method of any of embodiments 11-12, wherein the salt is selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, more preferably NaCl.
14. The method of any of embodiments 11-13, wherein the total concentration of the at least one salt is 0.01-5% w/w, preferably 0.015-4% w/w, more preferably 0.02-3% w/w or 0.1-2% w/w.
15. The method of any of embodiments 11-14, wherein the lactase preparation has a lactase activity of 10-5000 LAU-B/g.
16. The method of any of embodiments 11-15, wherein the lactase has an amino acid sequence which is at least 50% identical to SEQ ID NO: 1.
17. The method of any of embodiments 11-16, wherein the lactase is a C-terminally truncated form of a lactase obtained from *Bifidobacterium*, preferably *Bifidobacterium bifidum*.
18. The method of any of embodiments 11-17, wherein the lactase has a C-terminal end corresponding to amino acid 1304 of SEQ ID NO: 1.
19. The method of any of embodiments 11-18, wherein the liquid lactase preparation further comprises a stabilizing formulation chemical at a concentration of 10-70% w/w, preferably 30-60% w/w.
20. The method of the preceding embodiment, wherein the stabilizing formulation chemical is a polyol, preferably a polyol selected among glycerol, sorbitol, monopropylene glycol, sucrose, glucose, galactose or lactose, more preferably glycerol.
21. The method of any of embodiments 11-20, wherein the lactase preparation has an improved filterability compared to a second liquid lactase preparation having the same composition except that it does not comprise the at least one salt.
22. The method of any of embodiments 11-21, wherein said sterile filtering is performed in-line within a production process of a dairy product.
23. A method of sterile filtering a liquid lactase preparation, which comprises the steps of:
   a. providing a liquid lactase preparation,
   b. adding to said liquid lactase preparation at least one salt having a monovalent or divalent cation, wherein the at least one salt is added at a concentration of at least 0.01% w/w of the lactase preparation which is to be sterile filtered, and
   c. sterile filtering the lactase preparation obtained in step b.
24. The method of embodiment 23, wherein the salt is a salt of $Na^+$, $K^+$, $NH_4^+$ or $Mg^{++}$.
25. The method of any of embodiments 23-24, wherein the salt is selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, more preferably NaCl.
26. The method of any of embodiments 23-25, wherein the total concentration of the at least one salt is 0.01-5% w/w, preferably 0.015-4% w/w, more preferably 0.02-3% w/w or 0.1-2% w/w.
27. The method of any of embodiments 23-26, wherein the lactase preparation has a lactase activity of 10-5000 LAU-B/g
28. The method of any of embodiments 23-27, wherein the lactase has an amino acid sequence which is at least 50% identical to SEQ ID NO: 1.
29. The method of any of embodiments 23-28, wherein the lactase is a C-terminally truncated form of a lactase obtained from *Bifidobacterium*, preferably *Bifidobacterium bifidum*.
30. The method of any of embodiments 23-29, wherein the lactase has a C-terminal end corresponding to amino acid 1304 of SEQ ID NO: 1.
31. The method of any of embodiments 23-30, wherein the liquid lactase preparation further comprises a stabilizing formulation chemical at a concentration of 10-70% w/w, preferably 30-60% w/w.
32. The method of the preceding embodiment, wherein the stabilizing formulation chemical is a polyol, preferably a polyol selected among glycerol, sorbitol, monopropylene glycol, sucrose, glucose, galactose or lactose, more preferably glycerol.

33. The method of any of embodiments 23-32, wherein the lactase preparation has an improved filterability compared to a second liquid lactase preparation having the same composition except that it does not comprise the at least one salt.

34. The method of any of embodiments 23-33, wherein said sterile filtering is performed in-line within a production process of a dairy product.

35. A method of improving the filterability of a liquid lactase preparation, which comprises addition to the lactase preparation of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, wherein the salt is added at a concentration of at least 0.01% w/w of the lactase preparation.

36. Use of at least one salt selected among NaCl, KCl, $NH_4Cl$, $MgCl_2$, $Na_2SO_4$, $K_2SO_4$, $(NH_4)_2SO_4$, $MgSO_4$ or a combination thereof, preferably, NaCl, KCl, $MgCl_2$, $(NH_4)_2SO_4$, $Na_2SO_4$ or a combination thereof, for improving the filterability of a liquid lactase preparation.

FURTHER PREFERRED EMBODIMENTS

1. A sterile-filtered liquid lactase preparation comprising at least one salt having a monovalent cation, wherein the total concentration of said at least one salt is at least 0.01% w/w.

2. The liquid lactase preparation of embodiment 1, wherein the salt is a salt of $Na^+$, $K^+$ or $NH_4^{3O}$.

3. The liquid lactase preparation of embodiment 1, wherein the salt is selected among NaCl, KCl, $NH_4Cl$, $Na_2SO_4$, $K_2SO_4$, $(NH_4)_2SO_4$, or a combination thereof, preferably, NaCl, KCl, $(NH_4)_2SO_4$, $Na_2SO_4$ or a combination thereof, more preferably NaCl.

4. The liquid lactase preparation of any of the preceding embodiments, wherein the total concentration of the at least one salt is 0.01-5% w/w, preferably 0.015-4% w/w, more preferably 0.02-3% w/w or 0.1-2% w/w.

5. The liquid lactase preparation of any of the preceding embodiments which further comprises a polyol, preferably a polyol selected among glycerol, sorbitol, monopropylene glycol, sucrose, glucose, galactose or lactose, or combinations thereof, more preferably glycerol, at a concentration of 10-70% w/w, preferably 30-60% w/w.

6. The liquid lactase preparation of any of the preceding embodiments, wherein the lactase has an amino acid sequence which is at least 50% identical to SEQ ID NO: 1.

7. The liquid lactase preparation of any of the preceding embodiments, wherein the lactase has a C-terminal end corresponding to amino acid 1304 of SEQ ID NO: 1.

8. The liquid lactase preparation of any of embodiments 1 to 7, further comprising at least one salt having a divalent cation, preferably at least one salt of $Mg^{++}$, or the liquid lactase preparation of any of embodiments 5 to 7, further comprising at least one salt having a divalent cation, preferably at least one salt of $Mg^{++}$ 9. A method of sterile filtering a liquid lactase preparation, which comprises the steps of:
   a. providing a liquid lactase preparation comprising at least one salt having a monovalent cation, wherein the total concentration of said at least one salt is at least 0.01% w/w, and
   b. sterile filtering said lactase preparation.

10. The method of embodiment 9, wherein the at least one salt is selected from a salt of $Na^+$, $K^+$ or $NH_4^+$.

11. The method of any of embodiments 9-10, wherein at least one salt is selected among NaCl, KCl, $NH_4Cl$, $Na_2SO_4$, $K_2SO_4$, $(NH_4)_2SO_4$ or a combination thereof, preferably, NaCl, KCl, $(NH_4)_2SO_4$, $Na_2SO_4$ or a combination thereof, more preferably NaCl.

12. The method of any of embodiments 9-11, wherein the total concentration of the at least one salt is 0.01-5% w/w, preferably 0.015-4% w/w, more preferably 0.02-3% w/w or 0.1-2% w/w.

13. The method of any of embodiments 9-12, wherein the lactase has an amino acid sequence which is at least 50% identical to SEQ ID NO: 1.

14. The method of any of embodiments 9-13, wherein the lactase preparation has an improved filterability compared to a second liquid lactase preparation having the same composition except that it does not comprise said at least one salt having a monovalent cation.

15. The method of any of embodiments 9-14, wherein said sterile filtering is performed in-line within a production process of a dairy product.

EXAMPLE 1

Improved Filterability of *Bifidobacterium bifidum* Lactase Through Sterile Filter as a Function of Salt Content An unstandardized enzyme concentrate of *B. bifidum* lactase (SEQ ID NO: 1) expressed in *Bacillus licheniformis* and that had been produced in large scale was chosen as start material. The unstandardized concentrate had been originally formulated in large scale with 66% w/w glycerol at pH 5.7. The total sodium, potassium, magnesium, chloride and sulphate ions were measured in the unstandardized concentrate by means of ICP-OES and Dionex™ IC, respectively.

| Method | Total ion concentration in the unstandardized concentrate [mg/kg] |
|---|---|
| Dionex ™ IC for total chloride | 123 |
| Dionex ™ IC for total sulphate | Below detection limit of 100 |
| ICP-OES for total magnesium | 17 |
| ICP-OES for total potassium | 50 |
| ICP-OES for total sodium | 42 |

The concentrate was then diluted with glycerol and water in absence or presence of different salts down to an enzyme concentration equivalent to 900 LAU-B/g lactase units: the unstandardized lactase concentrate was first pre-diluted with pure glycerol prior to adding salt as powder; a control sample did not contain added salt. Water was eventually added to a final volume of 1 L, as described in the table here below. The final glycerol concentration was 50% w/w in all samples. Upon dilution of the unstandardized lactase concentrate the cations and anions present in the concentrate were diluted so extensively that the total amount of ions leftover in the diluted samples was very low to negligible compared to the different salt added voluntarily in this experiment.

| Samples | Unstandardized lactase concentrate + glycerol [g] | Salt [g] | Cold tap water [g] |
|---|---|---|---|
| 900 LAU-B/g (control) | 575 | 0 | 425 |
| 900 LAU-B/g + 0.1% w/w NaCl | 575 | 1 | 424 |
| 900 LAU-B/g + 1% w/w NaCl | 575 | 10 | 415 |
| 900 LAU-B/g + 2% w/w NaCl | 575 | 20 | 405 |
| 900 LAU-B/g + 1% w/w $Na_2SO_4$ | 575 | 10 | 415 |
| 900 LAU-B/g + 1% w/w $(NH_4)_2SO_4$ | 575 | 10 | 415 |

-continued

| Samples | Unstandardized lactase concentrate + glycerol [g] | Salt [g] | Cold tap water [g] |
|---|---|---|---|
| 900 LAU-B/g + 1% w/w MgCl$_2$, 6 H$_2$O | 575 | 10 | 415 |
| 900 LAU-B/g + 1% w/w KCl | 575 | 10 | 415 |

The unstandardized lactase concentrate and the pure glycerol solution were both kept at temperatures between 5° C. and 10° C. prior to start. All salts tested here were food grade quality and supplied by Sigma Aldrich Corp. (St. Louis, Mo., USA). Thorough mixing was achieved with a magnetic stir bar under cold conditions (5-10° C.).

All diluted enzyme solutions were then sterile filtered on 47 mm Fluorodyne® II DFL membrane filter discs (Pall, Port Washington, N.Y., USA) with a cutoff of 0.2 μm. The filter discs were maintained in a 47 mm inline stainless steel filter holder (Sartorius, Göttingen, Germany) and the diluted enzyme solutions were pumped through the filters by means of a FilterTec normal flow filtration system (Parker Hannifin Corp., Oxnard, Calif., USA) under constant flow regime of 10 ml/min and until the system pressure reached a maximum of 1.8 bar. The filtrations were carried out at room temperature, within 30-60 min after diluting the unstandardized enzyme concentrate.

The table here below lists the volume $V_{max}$ of the different solutions that were needed to reach an arbitrary, maximum pressure set point of 1.8 bar in the filtration system. The volume $V_{max}$ of the "control" sample was set to 100%; the volumes for the other solutions are therefore proportional to the base 100.

| Samples | $V_{max}$ of filtrate to reach a system pressure of 1.8 bar [%] |
|---|---|
| 900 LAU-B/g (control) | 100 |
| 900 LAU-B/g + 0.1% w/w NaCl | 127 |
| 900 LAU-B/g + 1% w/w NaCl | 122 |
| 900 LAU-B/g + 2% w/w NaCl | 116 |
| 900 LAU-B/g + 1% w/w Na$_2$SO$_4$ | 115 |
| 900 LAU-B/g + 1% w/w (NH$_4$)$_2$SO$_4$ | 132 |
| 900 LAU-B/g + 1% w/w MgCl$_2$, 6 H$_2$O | 135 |

All 900 LAU-B/g lactase solutions containing salt tested here showed a measurable improvement in filterability through a sterile filter compared to the control sample: the volume $V_{max}$ of lactase solution needed to reach the maximum pressure set point was higher in all accounts.

EXAMPLE 2

Improved Filterability of *Bifidobacterium bifidum* Lactase Through Sterile Filter Under Very Low Salt Conditions An unstandardized enzyme concentrate of *B. bifidum* lactase (SEQ ID NO: 1) expressed in *Bacillus licheniformis* and that had been produced in large scale was chosen as start material. The unstandardized concentrate had been originally formulated in large scale with 66% w/w glycerol at pH 5.7.

The concentrate was then diluted with glycerol and water in absence or presence of sodium chloride down to an enzyme concentration equivalent to 900 LAU-B/g lactase units per gram: the unstandardized lactase concentrate was first pre-diluted with pure glycerol prior to adding salt as powder; a control sample did not contain added salt. Water was eventually added to a final volume of 1 L, as described in the table here below. The final glycerol concentration was 50% w/w in all samples. Upon dilution of the unstandardized lactase concentrate the cations and anions present were diluted so extensively that the total amount of ions leftover in the samples were very low to negligible compared to the different salt added voluntarily during this experiment.

| Samples | Unstandardized lactase concentrate + glycerol [g] | Salt [g] | Cold tap water [g] |
|---|---|---|---|
| 900 LAU-B/g (control) | 575 | 0 | 425 |
| 900 LAU-B/g + 0.01% w/w NaCl | 575 | 0.1 | 424.9 |
| 900 LAU-B/g + 0.1% w/w NaCl | 575 | 1 | 424 |

The unstandardized lactase concentrate and the pure glycerol solution were both kept at temperatures around 10° C. to 15° C. prior to start. All salts tested here were food grade quality and supplied by Sigma Aldrich Corp. (St. Louis, Mo., USA). Thorough mixing was achieved with a magnetic stir bar under midly cold conditions (15° C.) in a water bath.

All diluted enzyme solutions were then sterile filtered on 47 mm Fluorodyne® II DFL membrane filter discs (Pall, Port Washington, N.Y., USA) with a cutoff of 0.2 μm. The filter discs were maintained in a 47 mm inline stainless steel filter holder (Sartorius, Göttingen, Germany) and the diluted enzyme solutions were pumped through the filters by means of a FilterTec normal flow filtration system (Parker Hannifin Corp., Oxnard, Calif., USA) under constant flow regime of 10 ml/min and until the system pressure reached a maximum of 1.8 bar. The filtrations were carried out at room temperature, within 30-60 min after diluting the unstandardized enzyme concentrate.

The table here below lists the volume $V_{max}$ of the different solutions that was needed to reach an arbitrary, maximum pressure set point of 1.8 bar in the filtration system. The volume $V_{max}$ of the "control" sample was set to 100%; the volumes for the other solutions are therefore proportional to the base 100.

| Samples | $V_{max}$ of filtrate to reach a system pressure of 1.8 bar [%] |
|---|---|
| 900 LAU-B/g (control) | 100 |
| 900 LAU-B/g + 0.01% w/w NaCl | 105 |
| 900 LAU-B/g + 0.1% w/w NaCl | 120 |

The addition of a very low sodium chloride amount (0.01% w/w) to the lactase concentrate showed already a measurable improvement in filterability through a sterile filter compared to the control sample. The $V_{max}$ % for the sample containing 0.1% w/w NaCl is very close to the one observed in Example 1.

The invention claimed is:

1. A liquid composition comprising
   (a) a lactase, wherein the concentration of the lactase is 10-5000 LAU-B/g;
   (b) at least one salt selected from the group consisting of NaCl, KCl, NH$_4$Cl and a combination thereof, wherein the concentration of the at least one salt is 0.1-5% w/w; and
   (c) a polyol selected from the group consisting of glycerol, sorbitol, monopropylene glycol, sucrose, glucose, galactose, lactose, and a combination thereof, wherein the concentration of the polyol is 10-70% w/w;
   wherein the liquid composition is sterile-filtered.

2. The composition of claim 1, wherein the at least one salt is NaCl.

3. The composition of claim 1, wherein the at least one salt is KCl.

4. The composition of claim 1, wherein the at least one salt is NH$_4$Cl.

5. The composition of claim 1, wherein the concentration of the polyol is 30-60% w/w.

6. The composition of claim 2, wherein the concentration of the polyol is 30-60% w/w.

7. The composition of claim 3, wherein the concentration of the polyol is 30-60% w/w.

8. The composition of claim 4, wherein the concentration of the polyol is 30-60% w/w.

9. The composition of claim 5, wherein the polyol is glycerol.

10. The composition of claim 6, wherein the polyol is glycerol.

11. The composition of claim 7, wherein the polyol is glycerol.

12. The composition of claim 8, wherein the polyol is glycerol.

13. The composition of claim 1, wherein the lactase has an amino acid sequence which is at least 50% identical to SEQ ID NO: 1.

14. The composition of claim 13, wherein the lactase has a C-terminal end corresponding to amino acid 1304 of SEQ ID NO: 1.

15. The composition of claim 1, further comprising at least one second salt having a divalent cation.

16. The composition of claim 15, wherein the at least one second salt having a divalent cation is a salt of Mg$^{++}$.

17. The composition of claim 9, further comprising at least one second salt having a divalent cation.

18. The composition of claim 17, wherein the at least one second salt having a divalent cation is a salt of Mg$^{++}$.

19. A method of sterilizing a liquid lactase composition, comprising sterile filtering a liquid composition which comprises (a) a lactase, wherein the concentration of the lactase is 10-5000 LAU-B/g; (b) at least one salt selected from the group consisting of NaCl, KCl, NH$_4$Cl and a combination thereof, wherein the concentration of the at least one salt is 0.1-5% w/w; and (c) a polyol selected from the group consisting of glycerol, sorbitol, monopropylene glycol, sucrose, glucose, galactose, lactose, and a combination thereof, wherein the concentration of the polyol is 10-70% w/w.

20. The method of claim 19, wherein the sterile filtering is performed in-line within a production process of a dairy product.

* * * * *

UNITED STATES PATENT AND TRADEMARK OFFICE
CERTIFICATE OF CORRECTION

PATENT NO. : 11,576,393 B2
APPLICATION NO. : 16/473118
DATED : February 14, 2023
INVENTOR(S) : Hobel et al.

It is certified that error appears in the above-identified patent and that said Letters Patent is hereby corrected as shown below:

On the Title Page

Column 1, item (72) (Inventors), Line 1, delete "Cedric" and insert -- Cédric --.

Column 2, item (56) (Other Publications), Line 6, delete "ABF27152.1" and insert -- ABE27152.1 --.

Column 2, item (56) (Other Publications), Line 29, delete "Chern.," and insert -- Chem., --.

Column 2, item (56) (Other Publications), Line 39, delete "Nebpage" and insert -- Webpage --.

Page 2, Column 1, item (56) (Other Publications), Line 4, delete "a.l," and insert -- al., --.

In the Specification

Column 1, Line 57, delete "Tetrapak" and insert -- Tetra Pak --.

Column 1, Line 61, delete "Tetrapak" and insert -- Tetra Pak --.

Column 12, Line 48, delete "LAU-B/g" and insert -- LAU-B/g. --.

Column 13, Line 30, delete "$NH_4^{30}$." and insert -- $NH_4^+$. --.

Column 13, Line 56 (approx.), delete "$Mg^{++}$" and insert -- $Mg^{++}$. --.

Column 16, Line 28 (approx.), delete "midly" and insert -- mildly --.

Signed and Sealed this
Twenty-ninth Day of October, 2024

Katherine Kelly Vidal
*Director of the United States Patent and Trademark Office*